(12) United States Patent
Sheldon et al.

(10) Patent No.: US 11,357,412 B2
(45) Date of Patent: Jun. 14, 2022

(54) WEARABLE CARDIOVASCULAR MONITORING DEVICE

(71) Applicant: 42 HEALTH SENSOR HOLDINGS LTD., Calgary (CA)

(72) Inventors: Robert Sheldon, Calgary (CA); Daniel Roach, Calgary (CA)

(73) Assignee: 42 HEALTH SENSOR HOLDINGS LTD., Calgary (CA)

( * ) Notice: Subject to any disclaimer, the term of this patent is extended or adjusted under 35 U.S.C. 154(b) by 343 days.

(21) Appl. No.: 16/197,192

(22) Filed: Nov. 20, 2018

(65) Prior Publication Data

US 2020/0155017 A1 May 21, 2020

(51) Int. Cl.
*A61B 5/021* (2006.01)
*A61B 5/022* (2006.01)
*A61B 5/00* (2006.01)

(52) U.S. Cl.
CPC ...... *A61B 5/02141* (2013.01); *A61B 5/02241* (2013.01); *A61B 5/6815* (2013.01);
(Continued)

(58) Field of Classification Search
CPC ......... A61B 5/6817; A61B 5/11; A61B 18/20; A61B 5/0095; A61B 5/0059; A61B 5/412; A61B 5/415; A61B 5/416; A61B 5/418; A61B 5/6814; A61B 8/08; A61B 1/227; A61B 5/1076; A61B 5/065; A61B 2018/00642; A61B 2562/0219; A61B 5/14532; A61B 18/1815;
(Continued)

(56) References Cited

U.S. PATENT DOCUMENTS 3,412,729 A 11/1968 Smith
5,237,997 A * 8/1993 Greubel ............. A61B 5/02125
600/485

(Continued)

FOREIGN PATENT DOCUMENTS

CA 2523549 12/2004
CH 104127176 6/2014
(Continued)

OTHER PUBLICATIONS

Popovic, R.S., Hall Effect Devices, 2003, CRC Press, Series in Sensors, p. 9 (Year: 2003).*

(Continued)

*Primary Examiner* — Sean P Dougherty
*Assistant Examiner* — Jonathan E. Cooper
(74) *Attorney, Agent, or Firm* — Meunier Carlin & Curfman LLC

(57) ABSTRACT

An apparatus for monitoring blood pressure of a user comprises a clip having a base with two side members adapted to releasably receive a portion of a body of the user therebetween with an adjustable pressure pad mounted to one of the two side members, spaced apart from the other of two side members by a separation distance, a magnetic field sensor mounted to one of the two side members with a magnet mounted to the other of the two side members opposite to the magnetic field sensor and spaced apart by the separation distance, a motor operably connected to the adjustable pressure pad wherein the separation distance is selectably adjustable by the motor.

12 Claims, 6 Drawing Sheets

(52) U.S. Cl.
CPC ........ *A61B 5/6838* (2013.01); *A61B 5/02108* (2013.01); *A61B 2562/0223* (2013.01); *A61B 2562/0247* (2013.01)

(58) Field of Classification Search
CPC .... A61B 2034/2051; A61B 2050/0016; A61B 2050/0018; A61B 2090/0813; A61B 2090/401; A61B 34/20; A61B 5/6867; A61B 50/00; A61B 8/481; A61B 90/40; A61B 18/203; A61B 2017/00106; A61B 2018/00452; A61B 2018/20351; A61B 2018/20357; A61B 2018/20361; A61B 2018/207; A61B 2034/2048; A61B 2034/2055; A61B 2034/2063; A61B 2034/2065; A61B 2090/3958; A61B 2562/0223; A61B 5/02007; A61B 5/05; A61B 5/6816; A61B 5/7278; A61B 18/14; A61B 2017/00022; A61B 2018/00476; A61B 2034/2059; A61B 2090/373; A61B 2090/378; A61B 2090/395; A61B 2503/40; A61B 5/1121; A61B 5/165; A61B 5/6803; A61B 7/04; A61B 2560/0219; A61B 2562/0204; A61B 2562/0233; A61B 3/113; A61B 5/0002; A61B 5/01; A61B 5/02438; A61B 5/04008; A61B 5/0476; A61B 5/062; A61B 5/0816; A61B 5/121; A61B 5/125; A61B 5/14546; A61B 5/228; A61B 5/6815; A61B 5/686; A61B 5/7257; A61B 18/24; A61B 2017/22038; A61B 2018/00327; A61B 2018/00577; A61B 2018/00636; A61B 2018/00672; A61B 2018/00904; A61B 2018/00982; A61B 2090/0805; A61B 2560/0252; A61B 2562/0247; A61B 2562/0285; A61B 2562/029; A61B 2562/063; A61B 2562/066; A61B 5/0004; A61B 5/0036; A61B 5/02028; A61B 5/0205; A61B 5/02055; A61B 5/021; A61B 5/02108; A61B 5/02405; A61B 5/0245; A61B 5/04012; A61B 5/0402; A61B 5/0404; A61B 5/04085; A61B 5/0478; A61B 5/04842; A61B 5/053; A61B 5/0533; A61B 5/06; A61B 5/0833; A61B 5/1118; A61B 5/12; A61B 5/14503; A61B 5/14525; A61B 5/14539; A61B 5/4842; A61B 5/4848; A61B 5/6838; A61B 5/6852; A61B 5/7264; A61B 5/7405; A61B 5/742; A61B 5/7455; A61B 5/7475; A61B 7/00; A61B 7/02; A61B 8/06; A61B 8/085; A61B 8/4281; A61B 8/4477; A61B 90/06; A61B 90/14; A61B 5/02141; A61B 5/022; A61B 5/02241; A61B 2560/0223; A61B 5/04005; A61B 5/04007; A61B 5/04009; A61K 49/22; A61K 49/225; A61K 38/15; A61K 41/00; A61K 41/0028; A61K 41/0042; A61K 41/0052; A61K 47/551; A61K 47/60; A61K 47/6849; A61K 49/221; A61K 9/1611; A61K 9/1641; A61K 9/1658; A61K 9/1676; A61M 2205/3303; A61M 2205/1726; A61M 2202/0225; A61M 2205/3324; A61M 3/0208; A61M 5/1723; A61M 5/007; A61M 1/1005; A61M 1/1008; A61M 1/101; A61M 1/1029; A61M 1/1031; A61M 1/1037; A61M 1/1039; A61M 1/1049; A61M 1/1055; A61M 1/1056; A61M 1/1058; A61M 1/106; A61M 1/1067; A61M 1/1072; A61M 1/1081; A61M 1/1084; A61M 1/1086; A61M 1/1098; A61M 1/12; A61M 1/122; A61M 1/125; A61M 1/3618; A61M 1/3683; A61M 2202/203; A61M 2205/0266; A61M 2205/0283; A61M 2205/0294; A61M 2205/04; A61M 2205/33; A61M 2205/3306; A61M 2205/3334; A61M 2205/336; A61M 2205/3375; A61M 2230/04; A61M 2230/10; A61M 2230/201; A61M 2230/205; A61M 2230/208; A61M 2230/432; A61M 2230/50; A61M 2230/63; A61M 2230/65; A61M 25/00; A61M 25/0127; A61N 1/36038; A61N 1/30; A61N 1/36036; A61N 1/37211; A61N 1/375; A61N 1/40; A61N 2/002; A61N 2/02; A61N 5/062; A61N 1/0541; A61N 2/004; A61N 1/3702; A61N 1/37217; A61N 1/37223; A61N 2/006; A61N 2/008; A61N 2005/067; A61N 5/0624; G01R 33/02; G01R 33/07

See application file for complete search history.

(56) References Cited

U.S. PATENT DOCUMENTS

| | | | |
|---|---|---|---|
| 5,316,008 A | 5/1994 | Suga et al. | |
| 5,649,543 A | 7/1997 | Hosaka et al. | |
| 5,857,975 A | 1/1999 | Golub | |
| 5,865,755 A | 2/1999 | Golub | |
| 6,198,394 B1 | 3/2001 | Jacobsen et al. | |
| 6,556,852 B1 | 4/2003 | Schulze et al. | |
| 7,539,532 B2 | 5/2009 | Tran | |
| 7,621,887 B2 | 11/2009 | Schnall | |
| 7,963,923 B2 | 6/2011 | Aihara et al. | |
| 8,437,826 B2 | 5/2013 | Chin | |
| 8,588,880 B2* | 11/2013 | Abdul-Hafiz | A61B 5/0261 600/344 |
| 8,632,471 B2 | 1/2014 | Lee et al. | |
| 8,968,195 B2 | 3/2015 | Tran | |
| 2002/0072681 A1* | 6/2002 | Schnall | A61B 5/02007 600/507 |
| 2003/0083559 A1 | 5/2003 | Thompson | |
| 2005/0113662 A1* | 5/2005 | Djennati | G01N 27/74 600/407 |
| 2006/0025701 A1* | 2/2006 | Kasahara | A61B 5/4872 600/547 |
| 2006/0253160 A1 | 11/2006 | Benditt et al. | |
| 2007/0070800 A1 | 3/2007 | Virag et al. | |
| 2007/0135717 A1 | 6/2007 | Uenishi et al. | |
| 2008/0319325 A1 | 12/2008 | Tatara et al. | |
| 2010/0013739 A1 | 1/2010 | Sako et al. | |
| 2010/0228103 A1 | 9/2010 | Schecter | |
| 2011/0066042 A1 | 3/2011 | Pandia et al. | |
| 2012/0046558 A1 | 2/2012 | Virag et al. | |
| 2016/0150984 A1* | 6/2016 | Kan | A61B 5/02116 600/490 |
| 2017/0012438 A1 | 4/2017 | Min et al. | |
| 2017/0156706 A1 | 6/2017 | Joseph et al. | |
| 2018/0078154 A1 | 3/2018 | Knickerbocker et al. | |
| 2018/0085057 A1* | 3/2018 | Lynde | A61B 5/02444 |

FOREIGN PATENT DOCUMENTS

| | | |
|---|---|---|
| CH | 105708431 | 4/2016 |
| WO | 9639927 | 12/1996 |
| WO | 2005110051 | 11/2005 |

(56) References Cited

FOREIGN PATENT DOCUMENTS

| WO | 2007026281 | 3/2007 | | |
|----|------------|--------|---|---|
| WO | 2007092543 | 8/2007 | | |
| WO | 2009036313 | 3/2009 | | |
| WO | WO-2009032074 A1 * | 3/2009 | ........... | A61B 5/6838 |
| WO | 2009147597 | 12/2009 | | |
| WO | 2010135518 | 11/2010 | | |
| WO | 2011076886 | 6/2011 | | |
| WO | 2011143490 | 11/2011 | | |
| WO | 2011161599 | 12/2011 | | |
| WO | 2012112891 | 8/2012 | | |
| WO | WO2015115114 A1 | 6/2015 | | |

OTHER PUBLICATIONS

Fraden, J., Handbook of Modern Sensors: Physics, Designs, and Applications, 2010, Springer New York, p. 73 (Year: 2010).*

Nam, D.; Lee, W.; Hong, Y.; Lee, S. Measurement of Spatial Pulse Wave Velocity by Using a Clip-Type Pulsimeter Equipped with a Hall Sensor and Photoplethysmography. Sensors 2013, 13(4), 4714-4723; (Year: 2013).*

International Search Report and Written Opinion, issued in corresponding Application No. PCT/IB2019/059941, dated Jan. 29, 2020, 8 pages.

\* cited by examiner

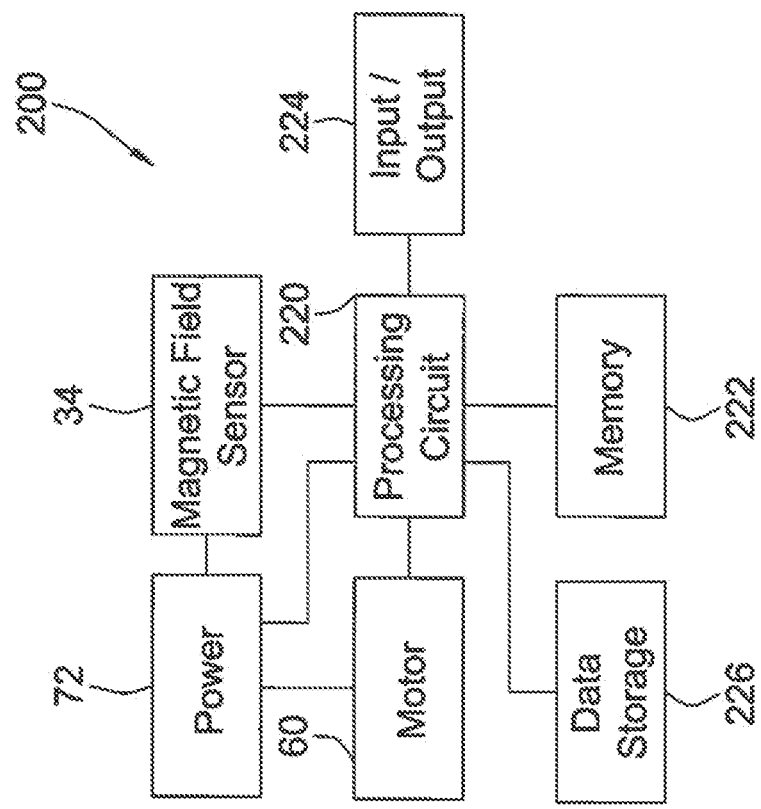
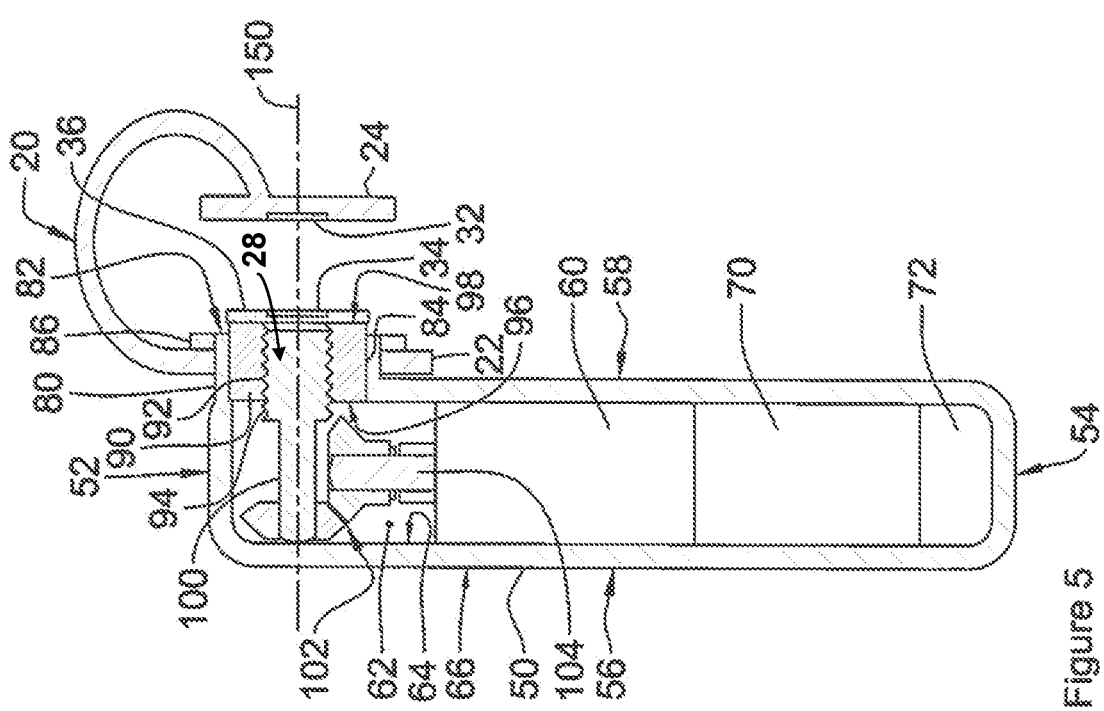

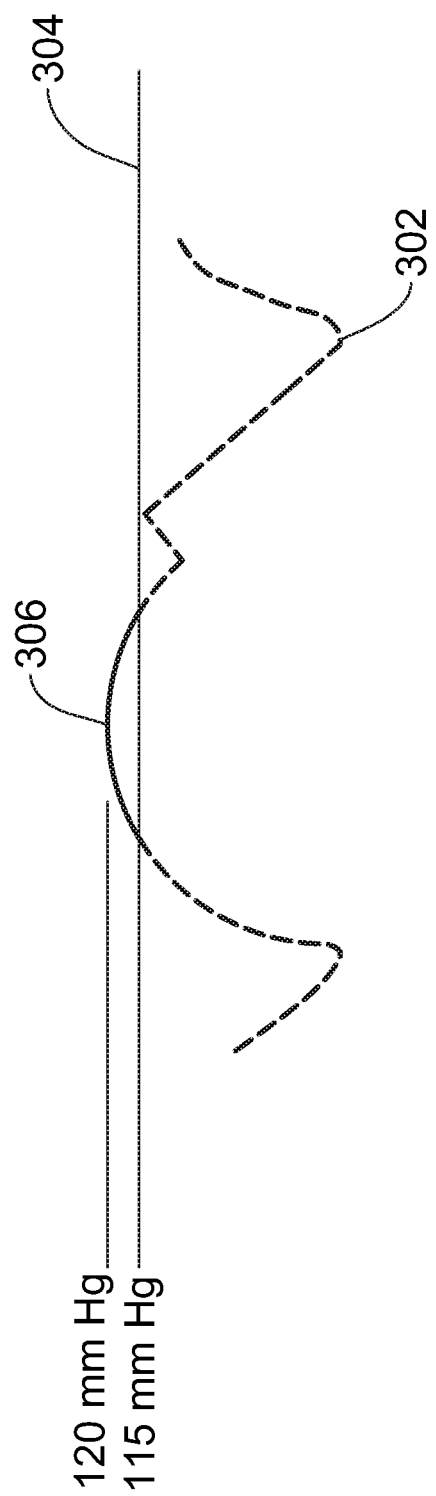

WEARABLE CARDIOVASCULAR MONITORING DEVICE

BACKGROUND OF THE INVENTION

1. Field of Invention

The present invention relates generally to physiological monitoring devices, and in particular to a wearable blood pressure monitoring device.

2. Description of Related Art

In order to diagnose or monitor a patient experiencing syncope or hypertension, a physician requires patient blood pressure (BP) data. A measurement taken by the physician during an in-clinic appointment captures only the patient's blood pressure at the time of the reading and does not detect transient changes in blood pressure throughout a typical day. Often the one-time reading is insufficient, and thus BP data collected over an extended period is ordered by the physician. Typically, this data is collected using an ambulatory blood pressure (BP) monitor over a period of 24 hours.

A standard ambulatory BP monitor consists of an automatically inflatable cuff worn on the user's arm for the diagnostic period, connected by an air supply tube to a monitoring device. These monitors are cumbersome to wear and interfere with normal activity as they automatically inflate and squeeze the user's arm to measure blood pressure approximately every 15 to 30 minutes of the day. It is recommended that the user limit movement and sit down, if possible, when the cuff is inflating and taking a reading. Disadvantageously, a user may not experience a typical day when interrupted regularly with an inflating cuff. Additionally, with measurements taken at a specified time interval, the data collected is a series of individual measurements, rather than a continuous, uninterrupted stream of data, thereby not truly providing full blood pressure data over the monitoring period for the patient.

Other devices have been proposed to measure blood pressure without an inflatable cuff. US Patent Application Publication No. 2007/0135717 to Uenishi et al. includes a pressure detection mechanism, however it does not allow for continuous measurement, but rather provides a single measurement similar to a blood pressure cuff.

SUMMARY OF THE INVENTION

According to a first embodiment of the present invention there is disclosed an apparatus for monitoring blood pressure of a user comprising a clip having a base with two side members adapted to releasably receive a portion of a body of the user therebetween with an adjustable pressure pad mounted to one of the two side members, spaced apart from the other of two side members by a separation distance, and a magnetic field sensor mounted to one of the two side members with a magnet mounted to the other of the two side members opposite to the magnetic field sensor and spaced apart by the separation distance. The apparatus further comprises a motor operably connected to the adjustable pressure pad wherein the separation distance is selectably adjustable by the motor.

The base of the clip may be generally formed in a U-shape. The clip may be sized to receive a portion of an ear of the user. The clip may be sized to receive a portion of a finger of the user.

The separation distance may be periodically reduced by the motor to apply pressure with the adjustable pressure pad to the portion of the user's body located between the adjustable pressure pad and the magnet. The magnet may comprise a rare earth magnet.

The magnetic field sensor may comprise a Hall effect sensor. The magnetic field sensor may be adapted to measure an arterial pulsatile waveform of blood flow within the portion of the body of the user located between the adjustable pressure pad and the magnet.

The apparatus may further comprise a processor in communication with the magnetic field sensor and the motor. The processor may monitor and record data from the magnetic field sensor. The processor may be configured to cause the motor to drive the adjustable pressure pad to periodically reduce the separation distance and apply a pressure with the adjustable pressure pad to the portion of the body of the user located between the adjustable pressure pad and the magnet. The processor may be configured to calibrate the data from the magnetic field sensor relative to the pressure.

According to a further embodiment of the present invention there is disclosed a method for monitoring blood pressure of a user comprising applying a clip having a magnetic field sensor and an opposed magnet thereon to a portion of a body of the user, measuring an arterial pulsatile waveform of blood flow within the portion of the body of the user located within the clip with the magnetic field sensor; and intermittently applying pressure to the portion of the body of the user located within the clip with an adjustable pressure pad.

The adjustable pressure pad may be operably connected to a motor. The motor may be activated by a processor in communication with the motor and the magnetic field sensor. The processor may convert the arterial pulsatile waveform of blood flow measurements from the magnetic field sensor to blood pressure measurement data. The processor may calibrate the blood pressure measurement data utilizing an adjusted arterial pulsatile waveform when the pressure is applied.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention wherein similar characters of reference denote corresponding parts in each view.

FIG. 5 is a cross sectional view of the apparatus of FIG. 1.

FIG. 6 is a block diagram of the control system for monitoring blood pressure of a user with the apparatus of FIG. 1.

FIG. 9 is an illustration of an adjusted blood pressure measurement as adjusted by the system of FIG. 6.

DETAILED DESCRIPTION

Figure 2:
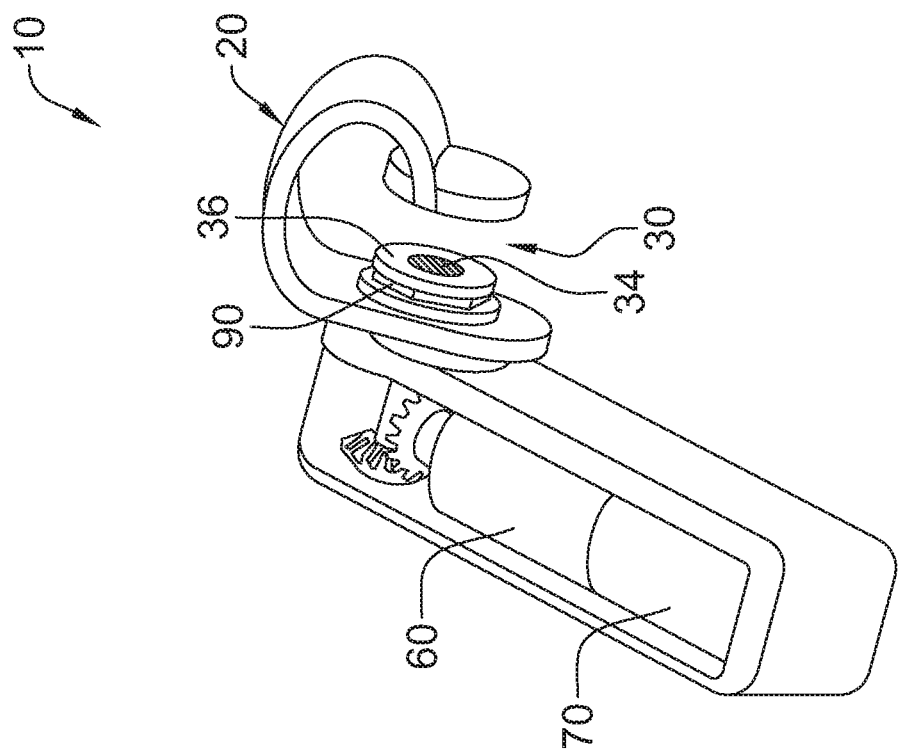
FIG. 2 is a perspective view of the apparatus of FIG. 1.
Figure 1:
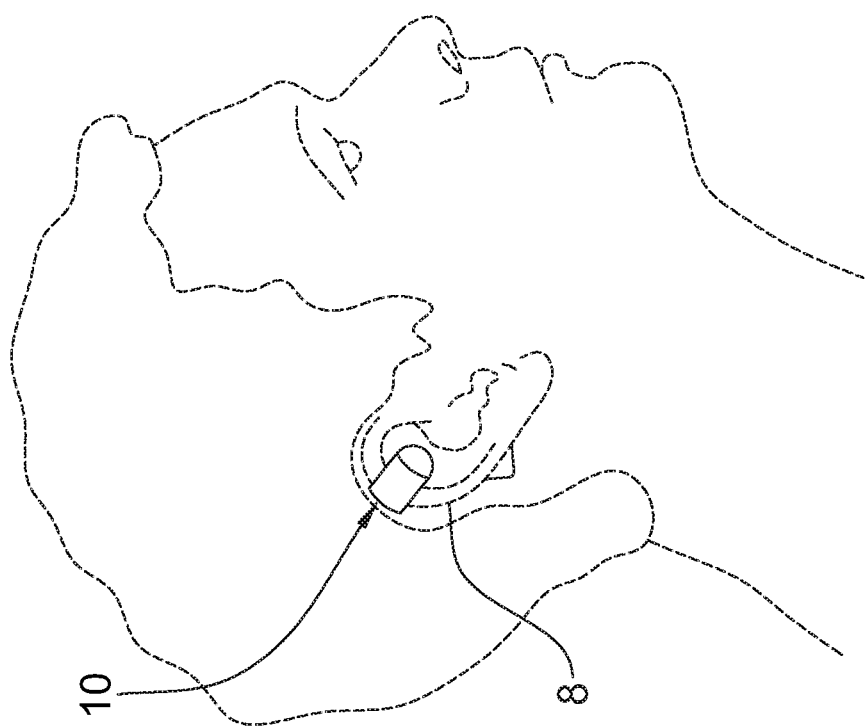
FIG. 1 is a side view of an apparatus for monitoring blood pressure of a user clipped to a portion of the user's ear.

Referring to FIGS. 1 and 2, an apparatus for monitoring blood pressure of a user according to a first embodiment of the invention is shown generally at 10, clipped to a portion of a user's ear 8. The apparatus 10 includes a clip 20 rotatably connected to a drive housing 50. The clip 20 is adapted to receive a portion of a user's ear 8 within a gap 30. A magnetic field sensor 34 mounted to an adjustable pressure pad 36 measures an arterial pulsatile waveform, as illustrated at 300 in FIG. 7 of blood flow within the ear 8 and sends the waveform measurements to a processor 70 within the drive housing 50, by means as are commonly known. A motor 60 within the drive housing 50 is operably connected to the adjustable pressure pad 36 and periodically extends and retracts the adjustable pressure pad 36 to calibrate the waveform measurements, as will be set out in more detail below. Although the present embodiment of the invention is illustrated clipped to an ear 8, it will be appreciated that the invention may be adapted to clip to other parts of a user's body, such as, by way of non-limiting example, a finger.

Figure 4:
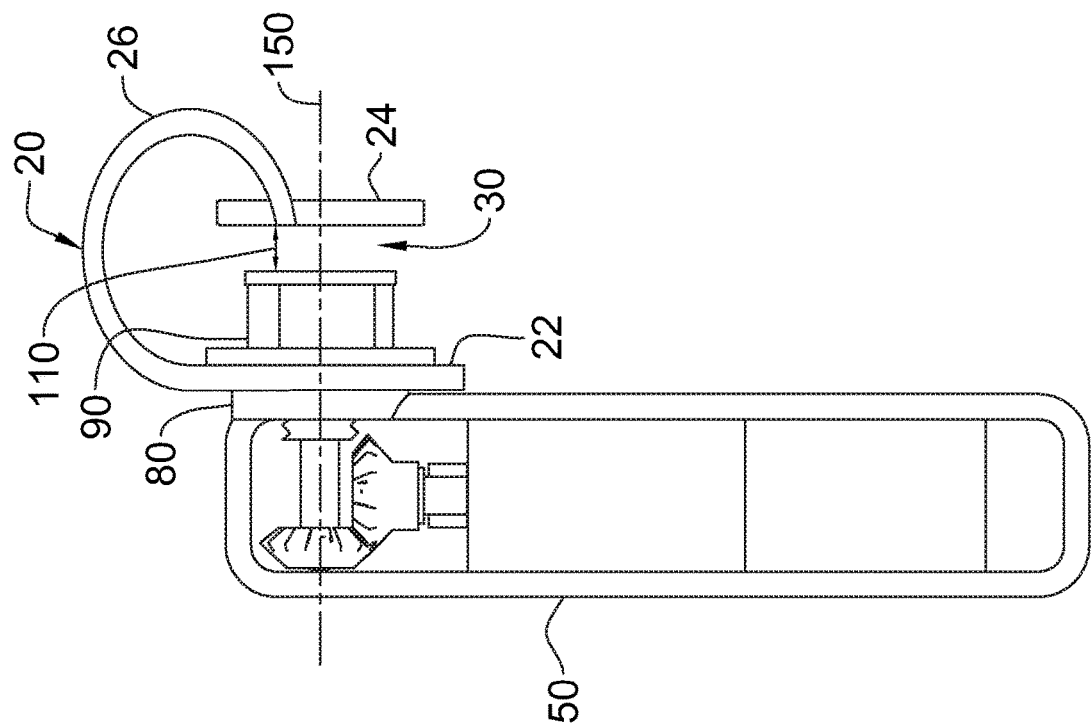
FIG. 4 is a side view of the apparatus of FIG. 1 with the adjustable pressure pad in an extended position.
Figure 3:
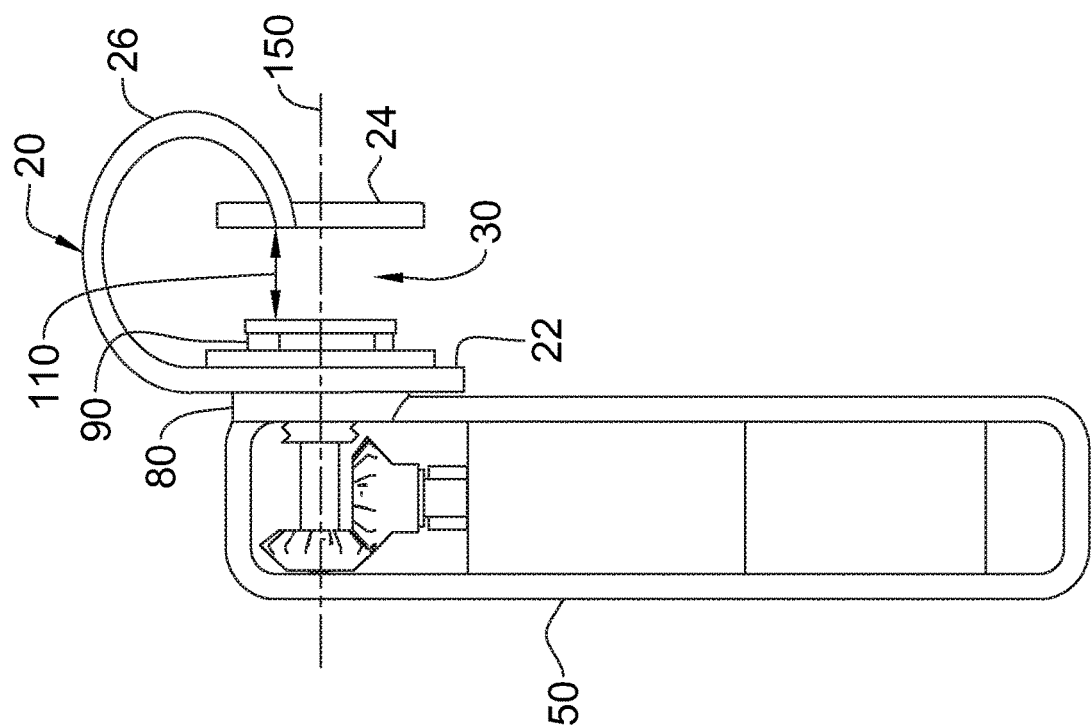
FIG. 3 is a side view of the apparatus of FIG. 1 with the adjustable pressure pad in a retracted position.

Turning now to FIGS. 3 through 5, the clip 20 includes first and second side members, 22 and 24, respectively, joined with a generally u-shaped base 26 forming the gap 30 therebetween. As set out above, the gap 30 is adapted to receive a portion of a user's ear 8 therein. The clip 20 is formed to accommodate varying sizes of connective tissue arch and the top of the ear cartilage of different users, as is commonly known. The clip 20 is formed with a rigid, non-ferrous material, so as to retain its shape when forces are applied thereto and to not vary the magnetic field at the magnetic field sensor 34.

As illustrated in FIG. 5, the first side member 22 includes a circular bore 28 on an axis 150 therethrough. The clip 20 is rotatably coupled to the drive housing 50 through the circular bore 28, as will be set out below.

The clip 20 includes a magnet 32 on the second side member 24, centred on the axis 150. As illustrated in FIG. 5, the magnet 32 may be retained within the second side member 24. The magnet 32 may be a rare earth magnet, such as, by way of non-limiting example, neodymium and samarium-cobalt magnets, as are commonly known, although other types of magnets may be useful as well. The magnetic field sensor 34 may be mounted within the adjustable pressure pad 36, as illustrated in FIG. 5, centered on the axis 150. The magnetic field sensor 34 may be a Hall effect sensor. As is commonly known, a Hall effect sensor requires an electric current for operation. A battery 72 is included in the drive housing 50. The magnetic field sensor 34 is connected to both the battery 72 and the processor 70 by means as are commonly known. Note that, for clarity, wiring is not shown on FIGS. 3-5. The magnet 32 provides a magnetic field for the magnetic field sensor 34 such that the magnetic field sensor 34 detects the interruption of the magnetic field by the blood flow of the user in the ear 8 therebetween.

Figure 7:
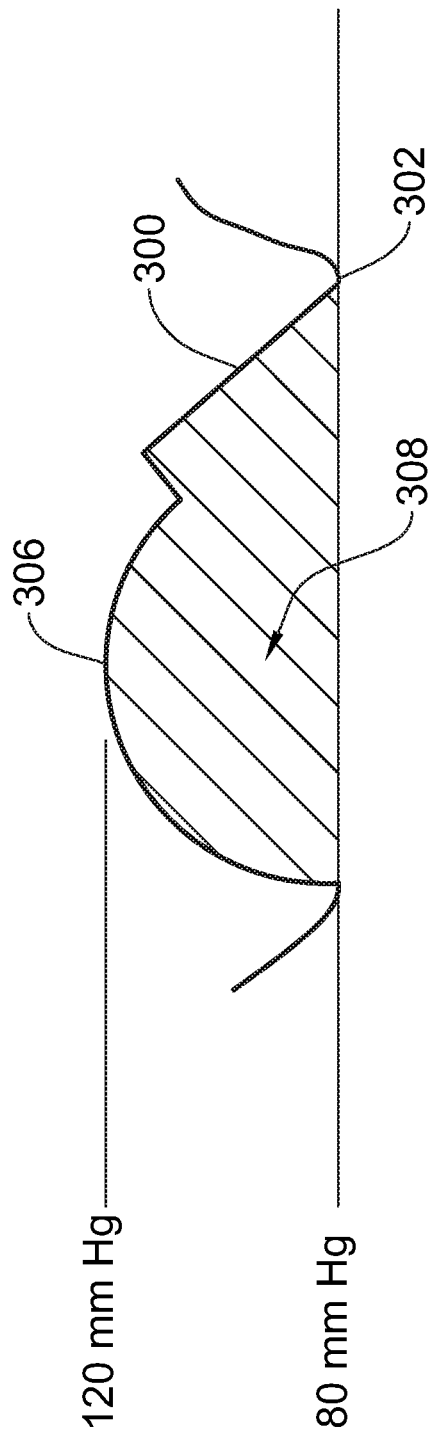
FIG. 7 is an illustration of an arterial pulsate waveform as measured by the apparatus of FIG. 1.

In operation, the amount of deflection within the clip 20 in response to an applied force may be known such that the change in width of the gap 30 is known in response to such force such that the effect on the measurements taken by the magnetic field sensor by a known amount. In particular it is known that magnetic field sensors are able to accurately measure distance to the magnetic source. Therefore, in operation, the clip 20 is located around the ear of the user such that the distance between the magnetic field sensor and the magnet 32 will vary in response to the blood flow through that portion of the ear. In particular, each pulse will cause the distance therebetween to increase. This distance is thereby measured and plotted to produce the arterial pulsate waveform as illustrated in FIG. 7. Optionally, the clip 20 may incorporate strain meters as are commonly known to measure the amount of deflection and therefore the change in the gap 30.

Referring to FIG. 5, the drive housing 50 is generally formed in a rounded rectangular box shape with an inside cavity 62 and has inner and outer surfaces 64 and 66, respectively. The drive housing 50 extends between top and bottom edges, 52 and 54, respectively, and between first and second sides, 56 and 58, respectively. It will be appreciated that the drive housing 50 may include front and back covers (not shown) to enclose the inside cavity 62 and protect the contents therein.

A cylindrical clip shaft portion 80 extends from the second side 58 of the drive housing 50 proximate to the top edge 52 along the axis 150 to a cylinder edge 82. The clip shaft portion 80 is adapted to rotatably receive the clip 20 thereon through the bore 28. A collar 86 is adapted to be received on the clip shaft portion 80 proximate to the cylinder edge 82 to retain the clip 20 on the clip shaft portion 80, as is commonly known. It will be appreciated that other retaining methods may be used to retain the clip 20 on the clip shaft portion 80, such as, by way of non-limiting example, a groove and retaining ring, a threaded collar, or adhesive. The clip 20 may be rotated about the axis 150 to adapt the apparatus 10 for varying ear sizes and shapes.

The clip shaft portion 80 includes a hexagonal bore 84 therethrough between the cylinder edge 82 and the inner surface 64 along the axis 150 adapted to receive a hexagonal extension nut 90 therein, as best illustrated in FIGS. 2-4. Although the bore 84 and extension nut 90 are illustrated as hexagonal in the current embodiment of the invention, it will be appreciated that other non-circular shapes may be useful, as well, such as, by way of non-limiting example, pentagonal or octagonal, such that the extension nut 90 does not rotate about the axis 150 within the bore 84. The extension nut extends between first and second ends, 96 and 98, respectively and includes internal threading 92 along the axis 150 adapted to engage with external threading 94 on a threaded driveshaft 100. The threaded driveshaft 100 is operably connected to the motor 60 through a pair of bevel gears 102 and a motor driveshaft 104, as is commonly known. The gears 102 and driveshafts 100 and 104 are formed with non-ferrous materials so that they do not interfere with the magnetic field sensor 34.

The adjustable pressure pad 36, with the magnetic field sensor 34 therein, is secured to the second end 98 of the extension nut 90. As set out above, the motor 60 is operably connected to the adjustable pressure pad 36 and periodically extends and retracts the adjustable pressure pad 36 to calibrate the waveform measurements, as will be set out below. The motor 60 rotates the motor driveshaft 104 thereby rotating the threaded driveshaft 100 via the gears 102. As the threaded driveshaft 100 is rotated, the engaged threading 92 and 94 extends the extension nut 90 from a retracted first position, as illustrated in FIG. 3, with a retracted separation distance 110 between the adjustable pressure pad 36 and the second side member 24, to an extended second position, as illustrated in FIG. 4, with an extended separation distance 110 between the adjustable pressure pad 36 and the second side member 24. As illustrated, the separation distance 110 is reduced when in the extended second position and is selected such that a predetermined force is applied to the ear 8 thereby producing a known blood pressure therethrough. As the extension nut 90 and bore 84 are non-circular, the extension nut 90 is not free to rotate within the bore 84 and therefore extends along the axis 150, as is commonly known.

Turning now to FIG. 6, the apparatus 10 includes a control system 200. The processor 70, illustrated previously in FIGS. 2 through 5, comprises a processing circuit 220 and memory 222 that stores machine instructions that, when executed by the processing circuit 220, cause the processing circuit 220 to perform one or more of the operations and methods described herein. The processing circuit 220 may optionally contain a cache memory unit for temporary storage of instructions, data, or computer addresses. The control system 200 further includes a data storage 226 of any conventional type operable to store a plurality of entries containing the waveform measurements received from the magnetic field sensor 34. It will be appreciated that the processing circuit 220 may contain instructions to convert the waveform measurements to blood pressure data, or the raw data received from the magnetic field sensor 34 may be stored within the data storage 226 and processed further into blood pressure data with a remote processor. Power is supplied to the magnetic field sensor 34 and processing circuit 220 with the motor 60 controlled by the processing circuit 220 to periodically extend and retract the adjustable pressure pad 36, as outline above. The control system 200 also includes an input/output interface 224 such as a radio transmitter, ethernet adapter, USB connection or the like for providing communication between the processing circuit 220 and external systems.

More generally, in this specification, including the claims, the term "processing circuit" is intended to broadly encompass any type of device or combination of devices capable of performing the functions described herein, including (without limitation) other types of microprocessing circuits, microcontrollers, other integrated circuits, other types of circuits or combinations of circuits, logic gates or gate arrays, or programmable devices of any sort, for example, either alone or in combination with other such devices located at the same location or remotely from each other. Additional types of processing circuit(s) will be apparent to those ordinarily skilled in the art upon review of this specification, and substitution of any such other types of processing circuit(s) is considered not to depart from the scope of the present invention as defined by the claims appended hereto. In various embodiments, the processing circuit 220 can be implemented as a single-chip, multiple chips and/or other electrical components including one or more integrated circuits and printed circuit boards.

Computer code comprising instructions for the processing circuit(s) 220 to carry out the various embodiments, aspects, features, etc. of the present disclosure may reside in the memory 222. In various embodiments, the processing circuit 220 can be implemented as a single-chip, multiple chips and/or other electrical components including one or more integrated circuits and printed circuit boards. The processing circuit 220 together with a suitable operating system may operate to execute instructions in the form of computer code and produce and use data. By way of example and not by way of limitation, the operating system may be Windows-based, Mac-based, or Unix or Linux-based, among other suitable operating systems. Operating systems are generally well known and will not be described in further detail here.

Memory 222 may include various tangible, non-transitory computer-readable media including Read-Only Memory (ROM) and/or Random-Access Memory (RAM). As is well known in the art, ROM acts to transfer data and instructions uni-directionally to the processing circuit 220, and RAM is used typically to transfer data and instructions in a bi-directional manner. In the various embodiments disclosed herein, RAM includes computer program instructions that when executed by the processing circuit 220 cause the processing circuit 220 to execute the program instructions described in greater detail below. More generally, the term "memory" as used herein encompasses one or more storage mediums and generally provides a place to store computer code (e.g., software and/or firmware) and data that are used by the control system 200. It may comprise, for example, electronic, optical, magnetic, or any other storage or transmission device capable of providing the processing circuit 220 with program instructions. Memory 222 may further include a floppy disk, CD-ROM, DVD, magnetic disk, memory chip, ASIC, FPGA, EEPROM, EPROM, flash memory, optical media, or any other suitable memory from which processing circuit 220 can read instructions in computer programming languages.

As set out above, the data storage 226 stores information for a plurality of waveform measurements from the magnetic field sensor 34. These measurements are periodically calibrated by activating the motor 60 to extend the adjustable pressure pad 36 for a set period of time such that a known pressure is applied to the portion of the ear 8 located between the adjustable pressure pad 36 and the second side member 24 of the clip 20 with the adjustable pressure pad 36 in the extended position, as illustrated in FIG. 4. As the pressure applied is known, and the resulting effect to the blood flow through the ear is known, the measurements may be calibrated to match a known pressure as applied by the motor 60. Once calibrated, the motor 60 is activated again to retract the adjustable pressure pad 36, returning the apparatus 10 to the retracted position, as illustrated in FIG. 3. It will be appreciated that the calibration of the measured arterial pulsatile waveform may be accomplished in many ways including arithmetic, geometric, modelled and spectal methods.

Figure 8:
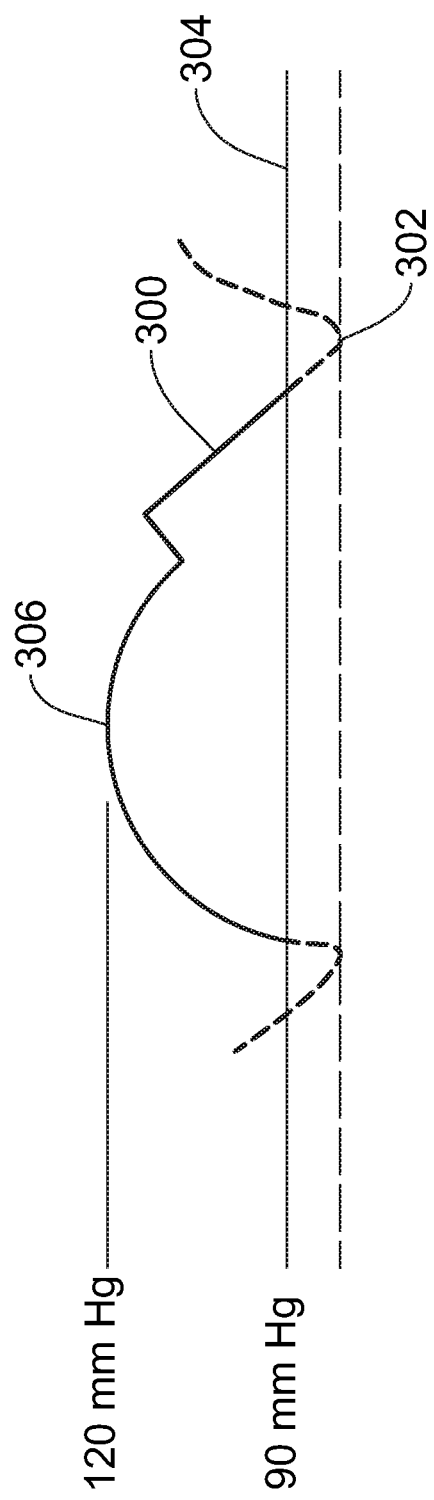
FIG. 8 is an illustration of an adjusted blood pressure measurement as adjusted by the system of FIG. 6.

By way of non-limiting example, the arterial pulsatile waveform 300 may be recorded as set out above and illustrated in FIG. 7 which includes a diastolic 302 and systolic pressure 306. As illustrated in FIG. 8, when the motor 60 is activated to apply a known pressure 304 as determined by the movement distance of the pressure pad 36. When the applied pressure is above the diastolic pressure 302 of the arterial pulsatile waveform 300 the measured diastolic pressure will no longer be recorded in arterial pulsatile waveform 300 and this diastolic pressure can therefore be adjusted to the applied pressure at that point. Similarly, as illustrated in FIG. 9, as the motor 60 applies a greater pressure 304 which approaches and exceeds the systolic pressure 306, the systolic pressure 306 of the arterial pulsatile waveform 300 will also be obscured such that the systolic pressure can then be calibrated to this known applied pressure 304.

Optionally, area (generally indicated at 308) under the arterial pulsatile waveform 300 may be measured to determine the volume of blood flow through the artery according to known methods. Furthermore, the apparatus 10 may be combined with one or more other sensors for use in monitoring the status of a patient including, breathing rate, oxygen saturation, activity level, temperature and whether the patient is awake or sleeping. Examples of such additional sensors may include without limitation, oximeters, tricolor LED/phototransistors, accelerometers, microphones, nasal thermistors, thermometers, skin galvanometers, linear photo transistor arrays, ultrasonic probes and arrays, infra-red LED/phototransistor pairs, RF impedance plethysmography and piezoelectric vibration elements.

Advantageously, when the apparatus as set out above is applied to the ear, it is known that the ear does not include any muscle therein. Additionally, the ear is not located at an extremity of the body which is significantly subjected to movement as is a hand or foot. Therefore, the measurements obtained from such location will not be dependent upon the movement and activity of the user. It will be appreciated that as the distance between the pad 36 and the magnetic field sensor 34 is known the volume of tissue between these surfaces is also known with a high degree of accuracy. Such accurate measurements of tissue volume may be useful for other purposes such as, by way of non-limiting example, measuring body fat percentages or water content.

While specific embodiments of the invention have been described and illustrated, such embodiments should be considered illustrative of the invention only and not as limiting the invention as construed in accordance with the accompanying claims.

What is claimed is:

1. An apparatus for monitoring blood pressure of a user comprising:
    a clip having a U-shaped base with two side members extending from the U-shaped base defining a fixed distance therebetween, the clip being adapted to releasably receive a portion of a body of the user therebetween, and the clip being formed from a rigid material that maintains the fixed distance therebetween when forces are applied thereto;
    an adjustable pressure pad mounted to one of said two side members spaced apart from the other of two side members by a separation distance;
    a magnetic field sensor mounted to one of said two side members;
    a magnet directly mounted to the other of said two side members opposite to said magnetic field sensor and spaced apart by said separation distance; and
    a motor operably connected to said adjustable pressure pad, the motor being operatively connected to said pressure pad by a threaded driveshaft, a pair of gears and a motor driveshaft,
    wherein said separation distance is selectably adjustable by said motor.

2. The apparatus of claim 1 wherein said clip is sized to receive a portion of an ear of the user.

3. The apparatus of claim 1 wherein said clip is sized to receive a portion of a finger of the user.

4. The apparatus of claim 1 wherein said separation distance is periodically reduced by said motor to apply pressure with said adjustable pressure pad to the portion of the user's body located between said adjustable pressure pad and said magnet.

5. The apparatus of claim 1 wherein said magnet comprises a rare earth magnet.

6. The apparatus of claim 1 wherein said magnetic field sensor comprises a Hall effect sensor.

7. The apparatus of claim 1 wherein said magnetic field sensor is adapted to measure an arterial pulsatile waveform of blood flow within the portion of the body of the user located between said adjustable pressure pad and said magnet.

8. The apparatus of claim 1 further comprising a processor in communication with said magnetic field sensor and said motor.

9. The apparatus of claim 8 wherein said processor monitors and records data from said magnetic field sensor.

10. The apparatus of claim 9 wherein said processor is configured to cause said motor to drive said adjustable pressure pad to periodically reduce said separation distance and apply a pressure with said adjustable pressure pad to the portion of the body of the user located between located between said adjustable pressure pad and said magnet.

11. The apparatus of claim 10 wherein said processor is configured to calibrate said data from said magnetic field sensor relative to said pressure.

12. The apparatus of claim 1, wherein the motor selectably adjusts said separation distance by rotating the motor driveshaft, which rotates the threaded driveshaft via the pair of gears.

* * * * *